US012662308B2

(12) United States Patent   (10) Patent No.:   US 12,662,308 B2
Bing et al.   (45) Date of Patent:   Jun. 23, 2026

(54) FEMININE PRODUCT DISPOSAL SYSTEM AND ASSOCIATED METHOD

(71) Applicant: Cintas Corporate Services, Inc., Cincinnati, OH (US)

(72) Inventors: Richard R. Bing, West Chester, OH (US); Megan Kathryn Helms, Hamilton, OH (US); David Steven Mesko, Wyoming, OH (US); Emily Yeager, Fort Thomas, KY (US); Pil Ho Chung, Palisades Park, NJ (US); Joshua Meador, Brooklyn, NY (US); Marco Perry, Brooklyn, NY (US); Brooke Williams, New York, NY (US)

(73) Assignee: Cintas Corporate Services, Inc., Cincinnati, OH (US)

( * ) Notice: Subject to any disclaimer, the term of this patent is extended or adjusted under 35 U.S.C. 154(b) by 68 days.

(21) Appl. No.: 18/460,729

(22) Filed: Sep. 5, 2023

(65) Prior Publication Data

US 2024/0076123 A1   Mar. 7, 2024

Related U.S. Application Data

(60) Provisional application No. 63/403,951, filed on Sep. 6, 2022.

(51) Int. Cl.
B65F 1/14   (2006.01)
A61F 13/551   (2006.01)
B65F 1/00   (2006.01)

(52) U.S. Cl.
CPC ........ B65F 1/1426 (2013.01); A61F 13/5515 (2013.01); B65F 1/0006 (2013.01);
(Continued)

(58) Field of Classification Search
CPC ........................... B65F 1/1426; B65F 1/0006; B65F 2210/126; B65F 2210/167; B65F 2210/196; B65F 2240/164; A61F 13/5515
(Continued)

(56) References Cited

U.S. PATENT DOCUMENTS 6,059,100 A   5/2000 Jones
6,739,114 B2   5/2004 Shaffer
(Continued)

FOREIGN PATENT DOCUMENTS

DE   20212283 U1   12/2003
GB   2520347 A   5/2015
WO   WO-2021145533 A1 *   7/2021

OTHER PUBLICATIONS

European Patent Office, Extended European Search Report issued in EP 23195736.6, dated Feb. 13, 2024 (8 pages).

*Primary Examiner* — Orlando E Aviles
*Assistant Examiner* — Niki M Eloshway
(74) *Attorney, Agent, or Firm* — FBT Gibbons LLP

(57) ABSTRACT

A sanitary product disposal container includes a container housing having a movable housing top cover. A cover hinge assembly allows the top cover to pivot between open and closed positions. Accordingly, a used feminine hygiene product may be placed in the interior space of the container housing in the open position of the housing top cover while minimizing touching the container housing to open the housing top cover. The housing may be selectively opened to facilitate removal of the used feminine hygiene products from the interior space all without exposure to the used products or the escape of unpleasant odors.

12 Claims, 17 Drawing Sheets

(52) U.S. Cl.
CPC ... *B65F 2210/126* (2013.01); *B65F 2210/167* (2013.01); *B65F 2210/196* (2013.01); *B65F 2240/164* (2013.01)

(58) Field of Classification Search
USPC ................................................... 220/495.06
See application file for complete search history.

(56) References Cited

U.S. PATENT DOCUMENTS

| | | | |
|---|---|---|---|
| 7,422,106 | B1 | 9/2008 | Kendra |
| 8,889,067 | B1 | 11/2014 | Weaver |
| 9,221,601 | B2 * | 12/2015 | Crawford .............. B65F 1/1638 |
| 9,375,366 | B1 | 6/2016 | Morisi |
| 11,103,390 | B2 * | 8/2021 | Lupia .................. A61F 13/5515 |
| 11,230,434 | B1 | 1/2022 | Sansone |
| 11,532,197 | B2 | 12/2022 | Coder et al. |
| 2005/0045650 | A1 * | 3/2005 | Tippman, Sr. ......... B65D 43/16 |
| | | | 220/828 |
| 2005/0098466 | A1 | 5/2005 | Thomas |
| 2007/0055213 | A1 | 3/2007 | Erekson |
| 2007/0295722 | A1 * | 12/2007 | Titas .................... B65F 1/1468 |
| | | | 220/23.83 |
| 2014/0332537 | A1 | 11/2014 | Goodfield |
| 2017/0029209 | A1 * | 2/2017 | Smith ................... B65F 1/1615 |
| 2017/0334641 | A1 * | 11/2017 | Chen ...................... B65F 1/068 |
| 2020/0087061 | A1 * | 3/2020 | Cole ......................... B65F 1/06 |
| 2020/0237583 | A1 * | 7/2020 | Lupia ..................... A61F 13/84 |
| 2021/0043023 | A1 | 2/2021 | Coder et al. |
| 2021/0229906 | A1 * | 7/2021 | Abang, Jr. ............. B65F 1/163 |

* cited by examiner

FEMININE PRODUCT DISPOSAL SYSTEM AND ASSOCIATED METHOD

This claims the benefit of U.S. Provisional Patent Application Ser. No. 63/403,951, filed Sep. 6, 2022 and hereby incorporated by reference in its entirety.

BACKGROUND OF THE INVENTION

This invention relates to a feminine product disposal system and associated method, and more particularly, to such a system which minimizes physical contact with the disposal system and viewing of the used products.

Disposal of feminine hygiene products, such as sanitary napkins, tampons, pads, and the like in a safe, sanitary, and discrete manner is often difficult. This issue may be particularly problematic in public restrooms which may not be equipped with proper disposal equipment. As such, some women may be tempted to flush the hygiene products down the toilet. However, disposal in the toilet may lead to sewage pipe blockages, which in turn may cause backups and overflow of plumbing components.

In view of the problems associated with flushing the feminine hygiene products down the toilet, women may also resort to disposal in a standard waste bin commonly found in public or private bathrooms. Although waste bin disposal avoids some of the plumbing issues noted above, disposal of the hygiene products into standard waste bins generally presents other problems, including foul odors and public health concerns, as the feminine hygiene product may become a source of infection and disease once it is soiled. Accordingly, placing used feminine hygiene products in a conventional open waste receptacle may result in the spread of bacteria as well as emanation of objectional odors from the waste receptacle to the surrounding areas.

In view of these deficiencies, special receptacles have been designed to alleviate at least some of the above-mentioned problems. However, many such receptacles do not provide a secure and controlled environment for the disposal of the hygiene products, as the container may be left open once the hygiene product has been deposited therein. Thus, odor and infection may emanate from the open container. Furthermore, such disposal receptacles tend to be large and take up a considerable amount of floor space, which in turn may create limited free space in the bathroom. In some instances, receptacles specifically designed for discarding feminine sanitary products may be found installed in washrooms, typically inside each restroom cubicle for users to make use of them privately. Many of these receptacles are wall-mounted and include a container having a self-closing hinged cover which can be manually opened by the user for the purpose of disposing a sanitary waste item into the container.

A problem with conventional feminine sanitary product disposal receptacles of this kind is that the cover becomes easily soiled when the user is depositing sanitary waste products into the container as the cover must be touched by the user. Consequently, germs and infectious organisms can easily be transferred to the next user of the disposal receptacle which can result in the spread of germs, increased risk of cross-contamination, and transmission of potential illness or disease. In addition, users have the feeling they are exposed to harmful agents by having to manually touch and operate the cover, and thus may easily feel uncomfortable when using conventional feminine sanitary product disposal receptacles.

Moreover, replacement of the bag within the disposal receptacle is unhygienic and tedious with known receptacles. Very often, the manipulation and operation of the receptacle to replace a filled bag with a fresh, empty bag is complicated and not intuitive for someone servicing the unit. Operation of known receptacles in this regard is often inconvenient and requires uncomfortable positioning for access to the interior of the receptacle. Manual manipulation of the receptacle by a user or service personnel typically risks cross-contamination and spread of germs and infectious organisms. Some known disposal receptacles of this type are automated with sensors in an attempt to alleviate physical contact with the receptacle. Unfortunately, such known receptacles have proven to be unreliable and often prone to malfunction.

Therefore, there is a need in the art for an easy-to-use feminine hygiene waste and storage container which allows for sanitary disposal of feminine hygiene products, which also mitigates the emission of odor from the disposed hygiene products. For example, a feminine sanitary product disposal receptacle is desired where the user feels there is little or no risk of making contact with bacteria and other harmful agents or allowing unpleasant odors to escape the disposal receptacle after disposing sanitary waste items into the container.

Various aspects of this invention address these particular needs and other needs, as will be disclosed in more detail below.

SUMMARY OF THE INVENTION

These and other objectives of this invention have been attained by various embodiments of this invention in which the disposal receptacle offers intuitive operation.

The receptacle in various embodiments limits visual access to the interior of the receptacle and disposed products contained therein while maintaining optimized access to the interior. The disposal receptacle of various embodiments of this invention reduces visual and physical contact while integrating intuitive and familiar process operation steps. Contact with the bag contained within the receptacle is limited and minimized and the bag is sealed prior to bag removal for enhanced protection of the service personnel.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

DETAILED DESCRIPTION OF THE INVENTION

Figure 1:
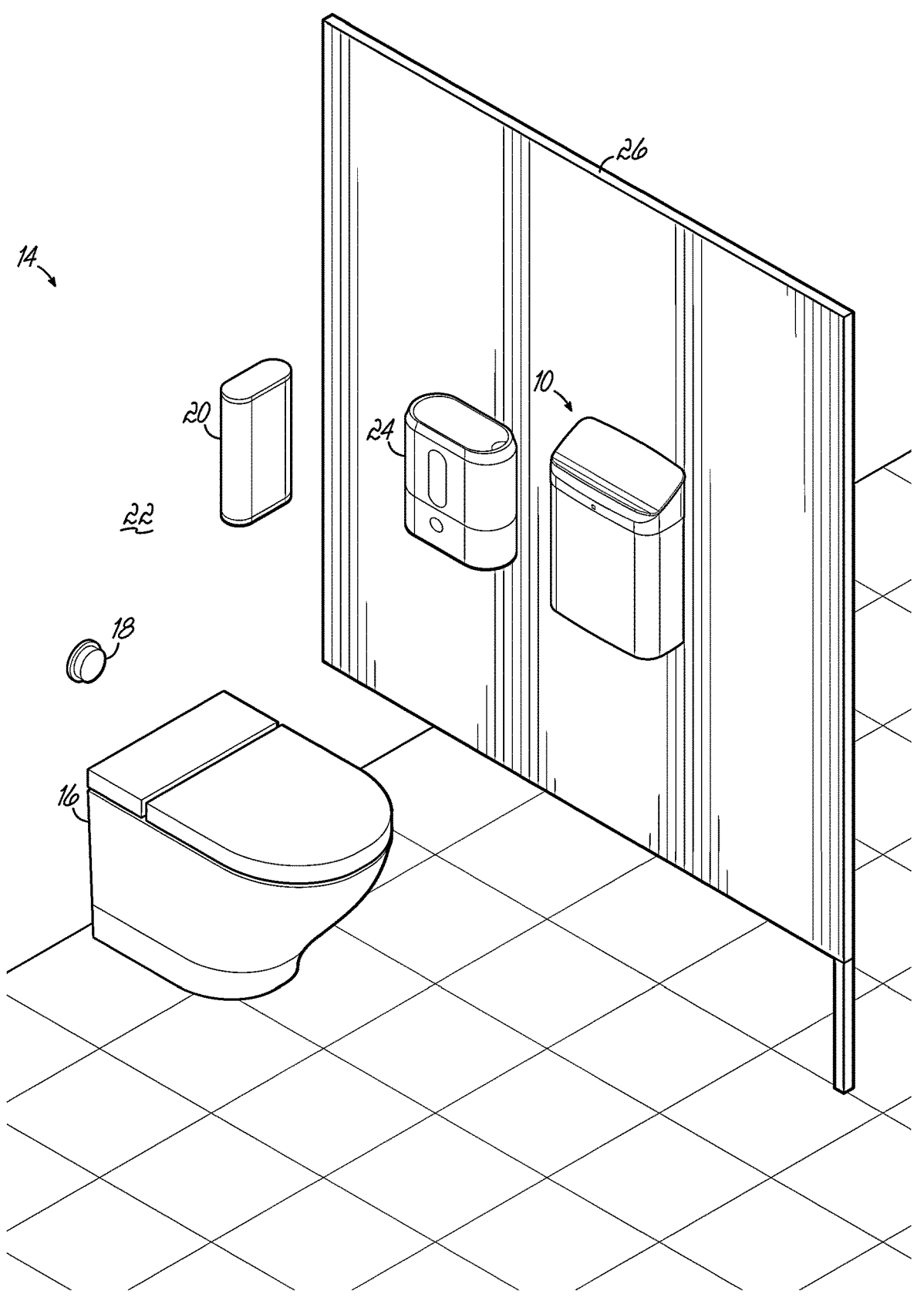
FIG. 1 is view of a typical bathroom environment in which a feminine product disposal receptacle according to various embodiments of this invention may be installed.

Referring to the drawings, an embodiment of a feminine product disposal receptacle 10 and associated disposal bags 12 to be used in association therewith are shown. The disposal receptacle 10 may be used in a private or public restroom 14, an example of which is shown in FIG. 1, which may include a commode 16, flush actuator 18 for the commode 16, hand sanitizer dispenser 20 mounted on a wall 22, feminine product dispenser 24 and privacy partitions 26. The feminine product disposal receptacle 10 may be mounted on the wall 22, partition 26 (as in FIG. 1) or any convenient location within the restroom 14. The various mounting surfaces associated with the disposal receptacle 10 will each present a generally vertical mounting plane and will be commonly referred to herein as a wall.

Figure 2:
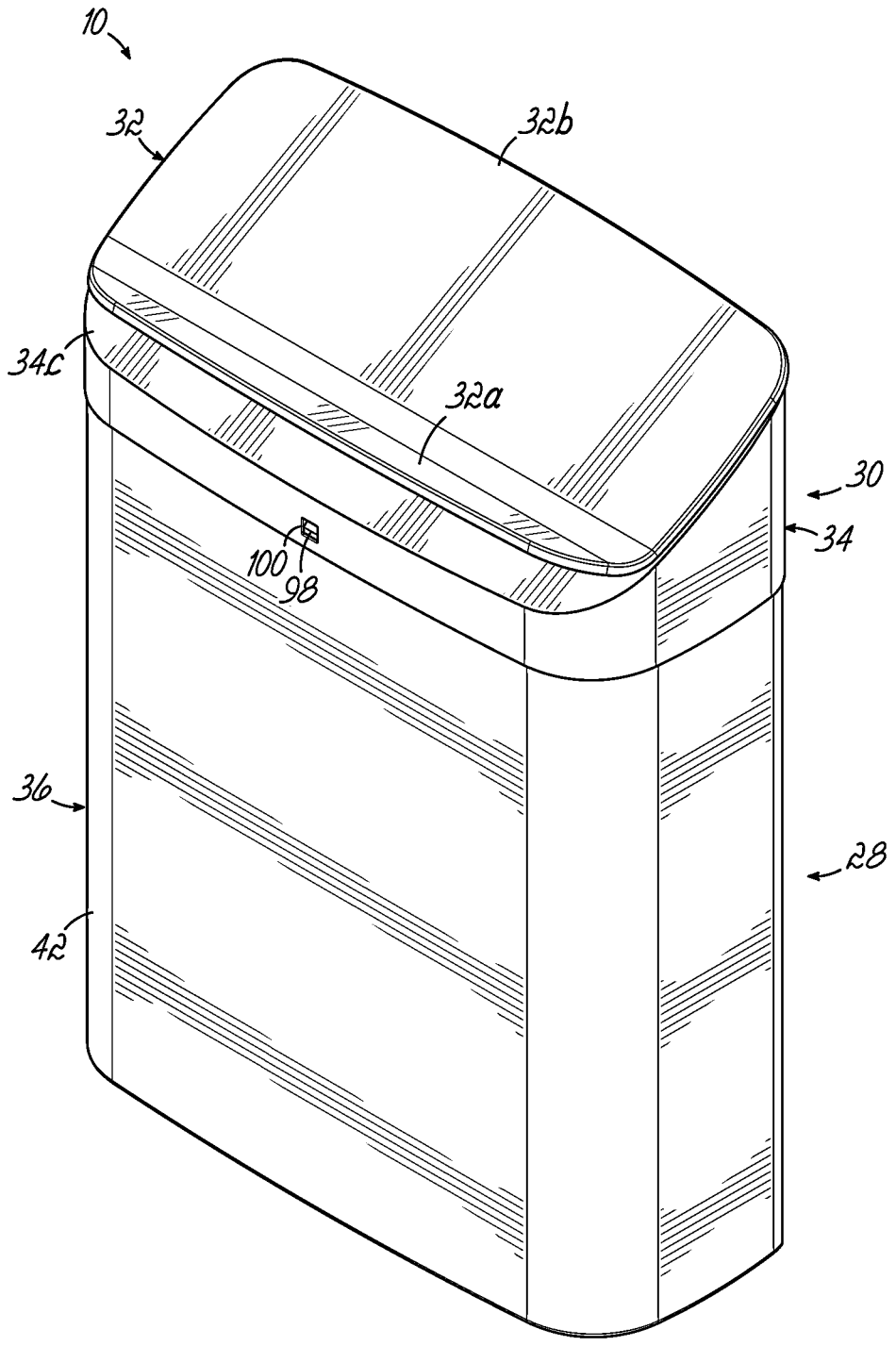
FIG. 2 is a perspective view of a first embodiment of the feminine product disposal receptacle according to this invention.
Figure 3:
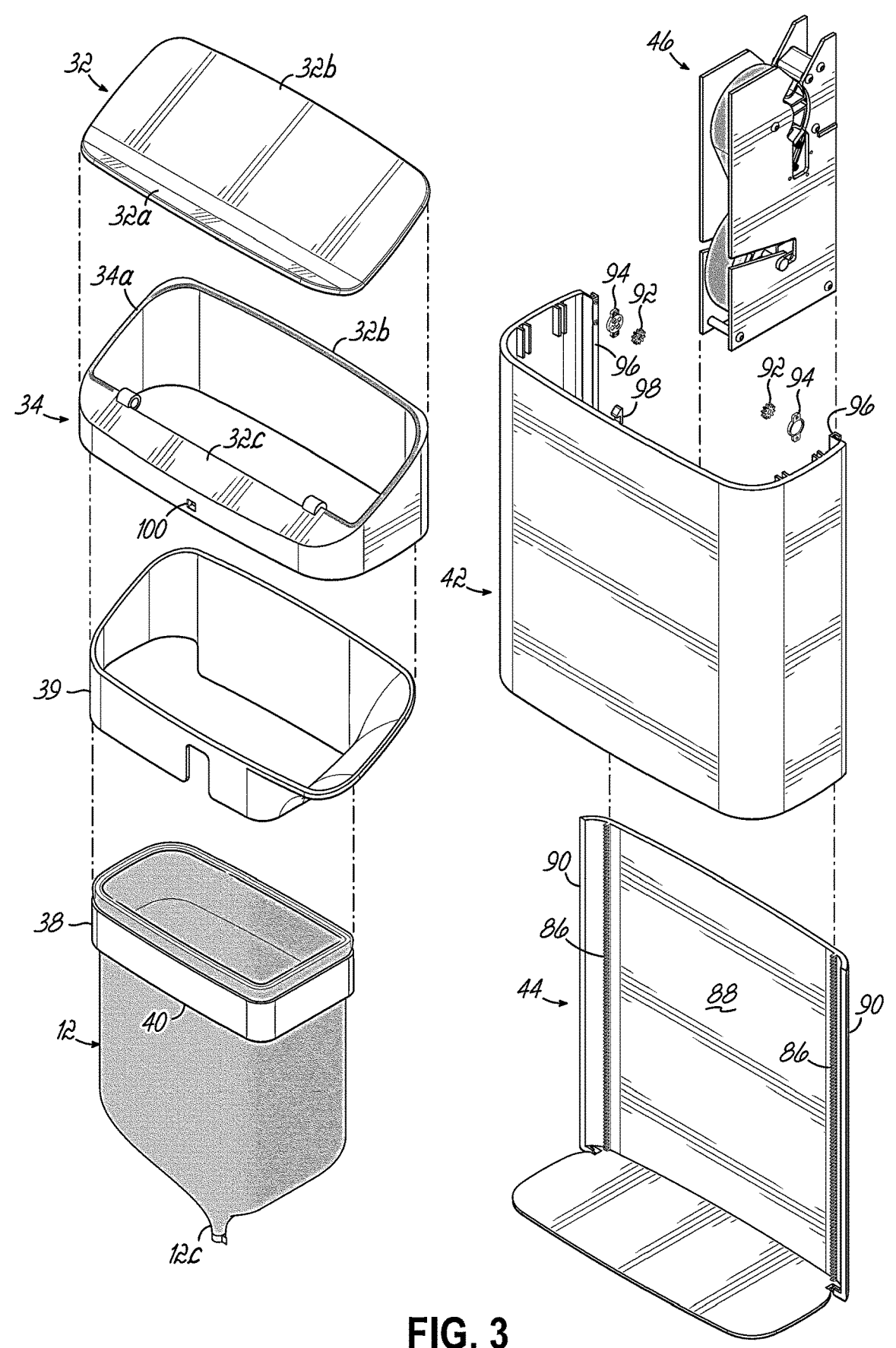
FIG. 3 is an exploded view of the embodiment of FIG. 2 showing the various components thereof.
Figure 5:
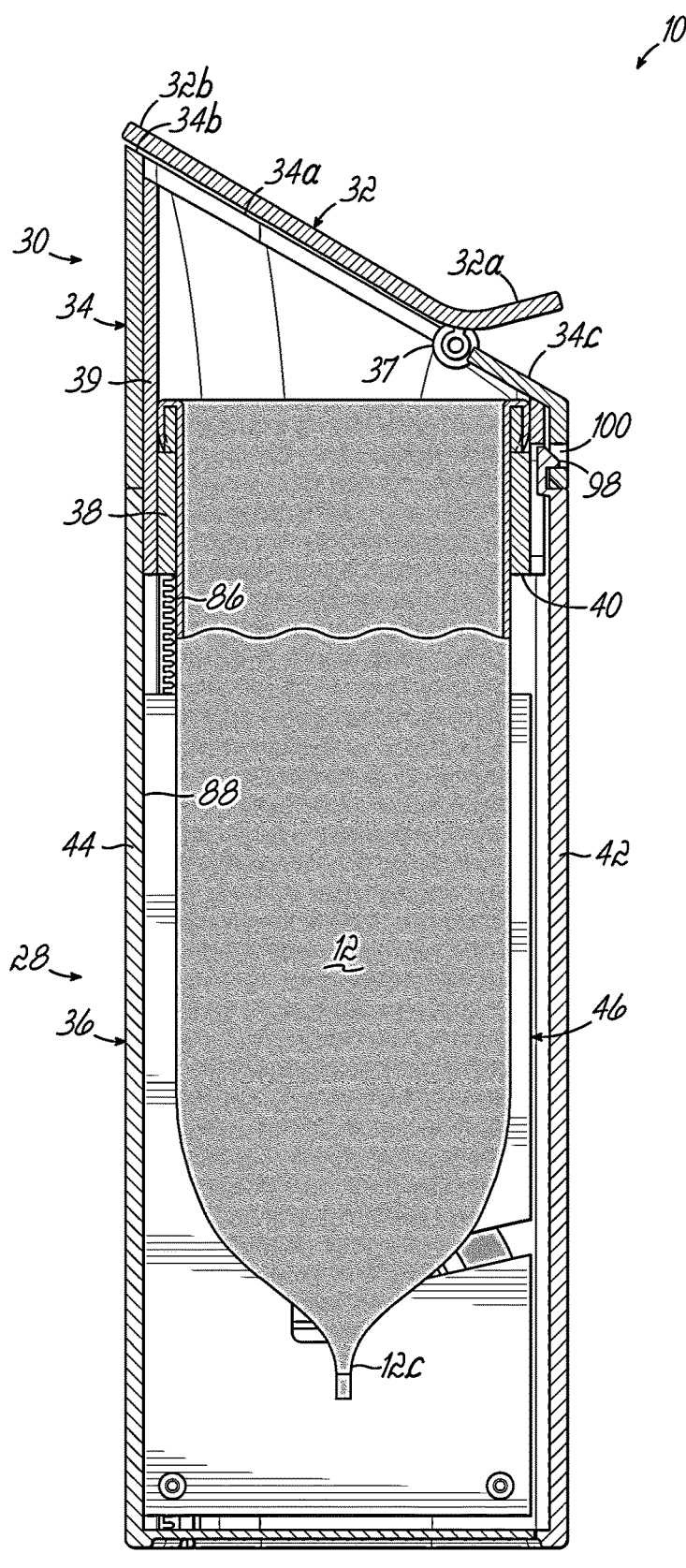
FIG. 5 is a cross-sectional side view of the embodiment of FIG. 2 with the lid in a closed position.
Figure 6:
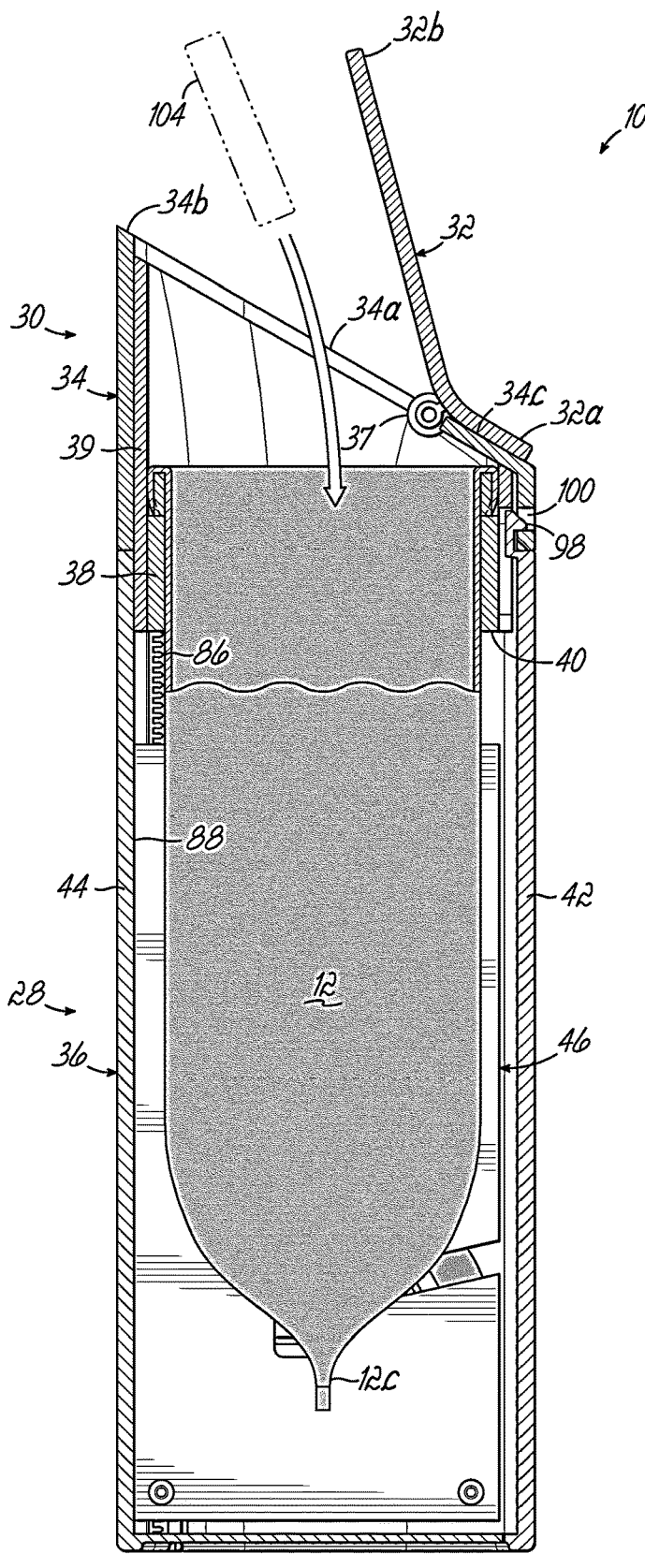
FIG. 6 is a cross-sectional side view of the embodiment of FIG. 2 with the lid in an open position with used product being deposited therein.
Figure 7:
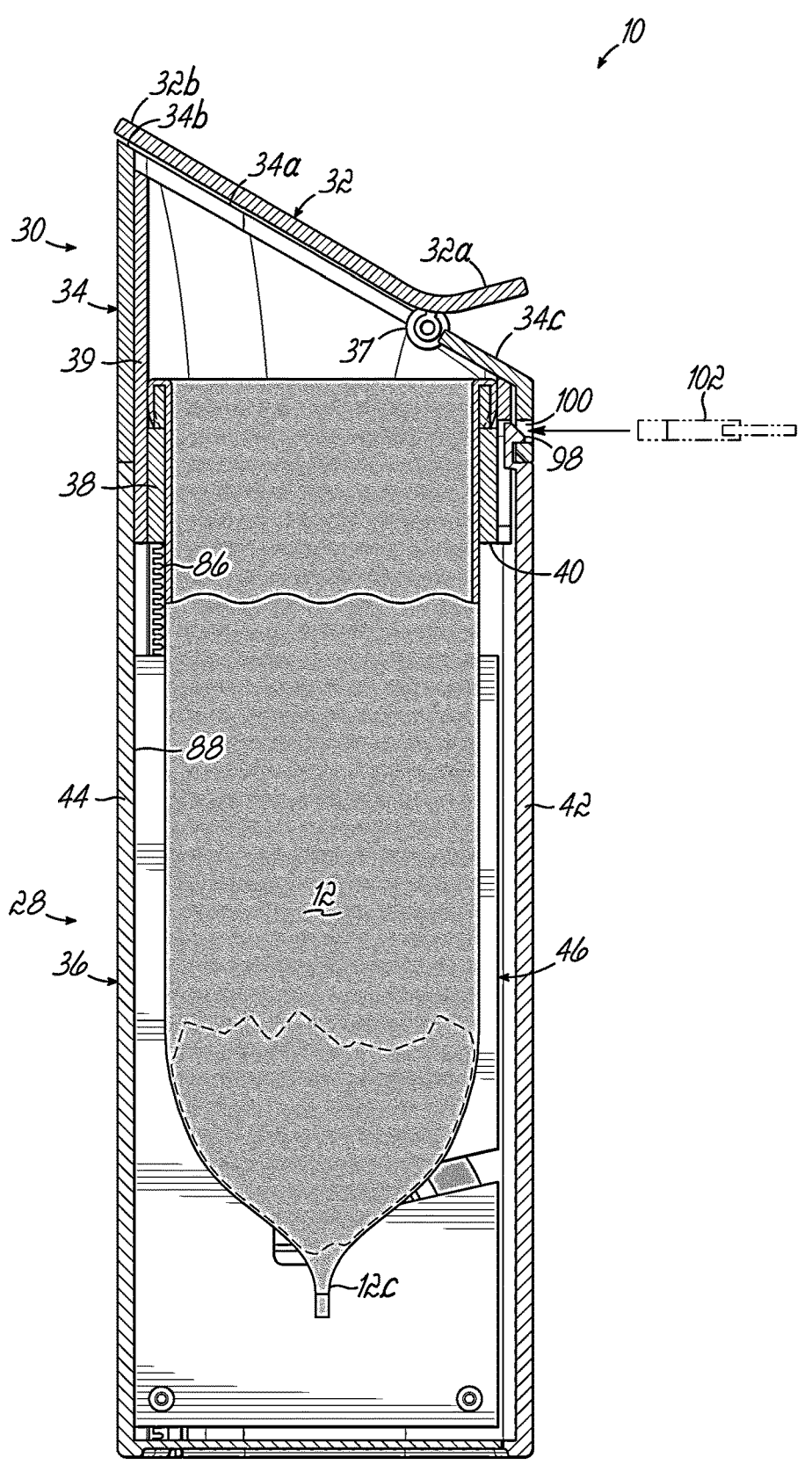
FIG. 7 is a view similar to FIG. 5 with a key being inserted to transform the disposal receptacle from a collapsed configuration as shown in FIGS. 2 & 5.
Figure 9:
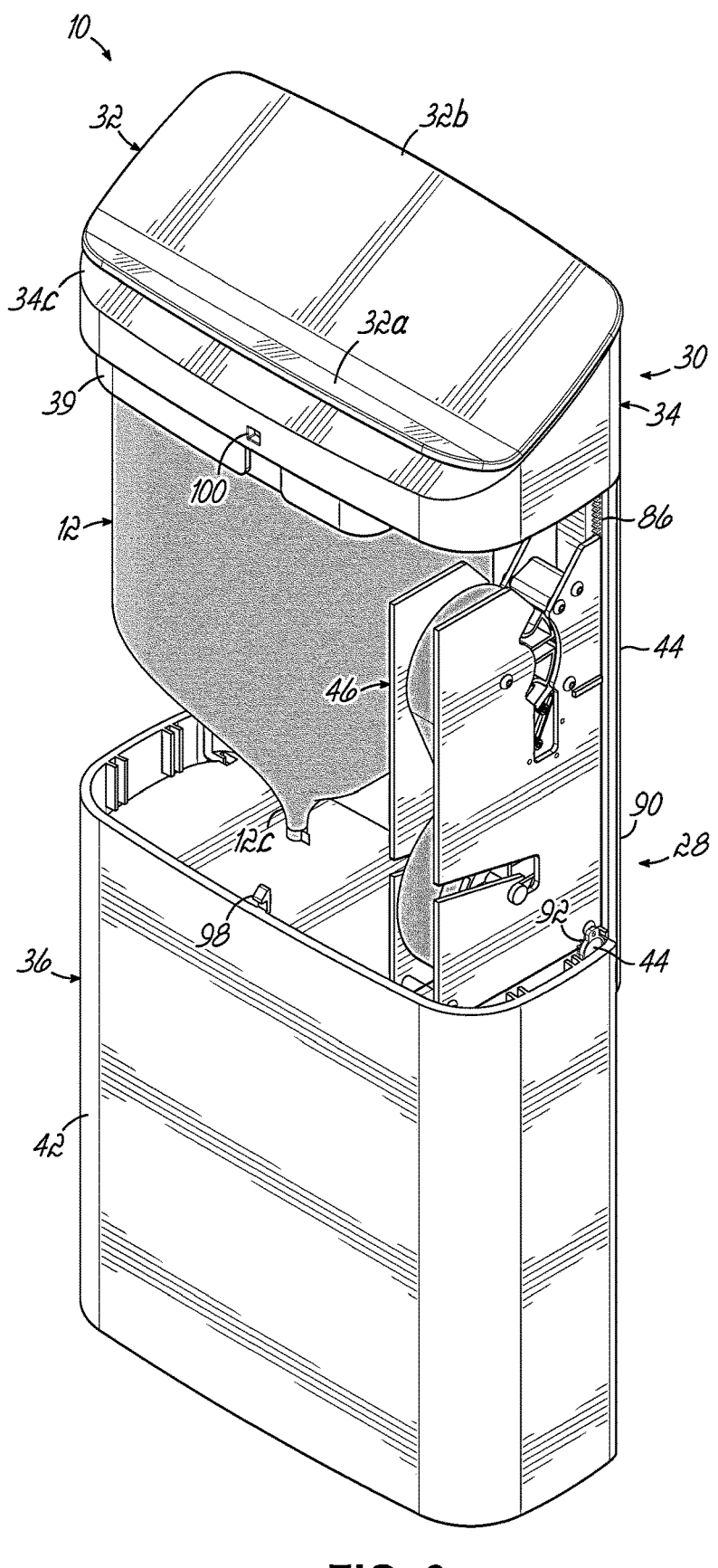
FIG. 9 is a perspective view of the disposal receptacle in the expanded configuration.

A first embodiment of the disposal receptacle 10 is shown in FIGS. 2-3 and 9 and includes a body assembly 28 and a lid assembly 30 mounted atop the body assembly 28. The disposal receptacle 10 may be mounted to the wall 22, the privacy partition 26 or another convenient location in the restroom 14 for disposal of feminine products 11 including sanitary napkins, tampons, pads, and the like in a safe and convenient manner. The lid assembly 30 includes a lid 32 pivotally mounted to a collar 34 extending upwardly from a body 36 of the receptacle 10. The lid assembly 30 also includes a lever portion 32a oriented in a different plane from a remainder of the lid 32 and directed forwardly from the lid 32 as shown in FIGS. 5-7. The collar 34 has an upper edge 34a which is tapered from an elevated portion 34b proximate a back of the receptacle 10 and the wall 22 when the receptacle is mounted thereto to a lower portion 34c proximate a front of the receptacle 10. The lid 32 is pivotally mounted for movement to and between an open position (FIG. 6) and a closed position (FIG. 2).

One feature of this embodiment of the receptacle 10 is that the lid 32 is pivotally mounted to the collar 34 by a barrel hinge 37 (FIGS. 5-8) located proximate the front of the receptacle 10 and the lower portion 34c of the collar 34 such that when the lid 32 pivots from the closed position, a back edge 32b of the lid 32 lifts from the elevated portion 34b of the collar 34 toward the open position. The hinge 37 is positioned proximate to a juncture between the lever portion 32a and the remainder of the lid 32. In other words, an opening to deposit soiled feminine products into the receptacle 10 is formed between the lid 32 in a generally upright orientation (FIG. 6) and the wall 22 when in the open position. The lever portion 32a maybe depressed by a user to open the lid assembly 30 into the open position without seeing or contacting the soiled feminine products already in the bag 12 in the receptacle 10. The combination of the location of the pivot axis of the barrel hinge 37 for the lid 32 proximate the front of the receptacle 10, the location of the wall 22 on which the receptacle 10 is mounted and the configuration of the collar 34 allows for this aspect of various embodiments of the invention. One advantage of this feature of the receptacle 10 is that a user is generally blocked from viewing the soiled products already in the receptacle 10 when depositing additional soiled products therein through the lid 32 in the open position. Moreover, contact with the contents of the receptacle 10 is inhibited with the lid 32 in the open position to thereby minimize a user's exposure to bacteria, other harmful agents and unpleasant odors within the receptacle 10.

Referring to FIG. 3, an exploded view of the components of this embodiment of the receptacle 10 is shown. The collar 34 is mounted on a rim 38 with an annular flange 39 of the lid assembly 30 therebetween. The collar 34, lid 32, annular flange 39 and rim 38 can be lifted from and replaced onto the body assembly 28 of the receptacle 10. The rim 38 may have a lip 40 formed at the lower edge thereof proximate an upper edge of a shell 42 of the body assembly 28. The shell 42 is a generally U-shaped member which is mounted to a generally L-shaped bracket 44 for vertical movement relative to the bracket 44 to and between a collapsed configuration (see FIG. 2) and an expanded configuration as show in FIG. 9.

Figure 4:
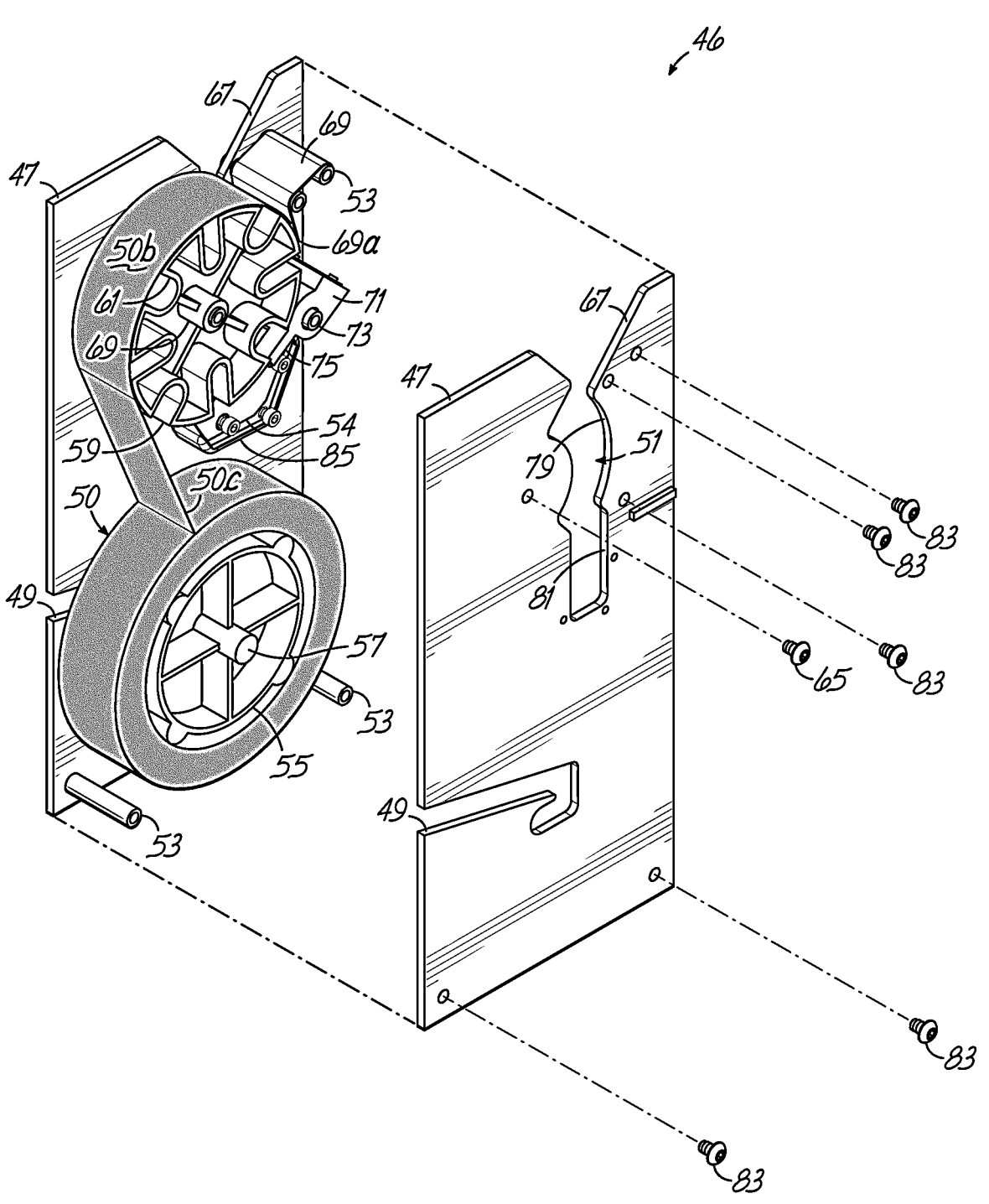
FIG. 4 is a perspective view of a tape and seal mechanism shown in the embodiment of FIGS. 2 & 3.

A tape cartridge 46 is located within the shell 42 as shown in FIG. 3. A partially disassembled perspective view of the tape cartridge 46 is shown in FIG. 4 which includes a pair of plates 47, 47 which are mirror images of one another. Each plate includes a J-shaped tape supply notch 49 and a bag sealing notch 51. The plates 47, 47 are held in spaced relation to one another when assembled together by a number of spacers 53 which receive screws to assemble the plates 47, 47 together. A tape supply spool 55 is sandwiched between the assembled plates 47, 47 and includes a center spindle 57 extending from each face of the supply spool 55 along a central axis of rotation of the supply spool 55. The ends of the spindle 57 are seated in the proximal end of the J-shaped notch 49 in each plate 47 to allow for rotation of the supply spool 55 between the plates 47, 47. A roll of tape 50 is mounted on the supply spool 55 and a terminal end portion 50a of the roll of tape 50 is mounted on the circumference of a sealing spool 59 as shown in FIG. 4. The tape 50 has an adhesive face 50b and a non-adhesive face 50c as is common. The sealing spool 59 includes a number of spaced notches 61 oriented radially on the spool 59 and open at the circumference of the spool 59. The non-adhesive face 50c is juxtaposed to the circumference of the sealing spool 59. The sealing spool 59 is mounted for rotation about central hub 63 thereof. A pair of screws 65 each passing through one of the plates 47 and into the central hub 63 mounts the sealing spool 59 for rotation between the plates 47, 47.

A throat 67 is formed at the upper edge of the bag seal notch 51 in each plate 47. A guide plate 69 is mounted between the plates 47, 47 adjacent to the throat 67 and opposite from the sealing spool 59. A tail 69a of the guide plate 69 extends downwardly and scrapes along the circumference of the sealing spool 59 as it rotates (see FIG. 15). A keeper boss 71 is pivotally mounted about a pin 73 between the plates 47, 47. The keeper boss 71 has a keeper arm 75 extending outwardly. The keeper arm 75 is biased by a spring 77 into contact with the circumference of the sealing spool 59 as it rotates in the direction of arrow A.

Figure 15:
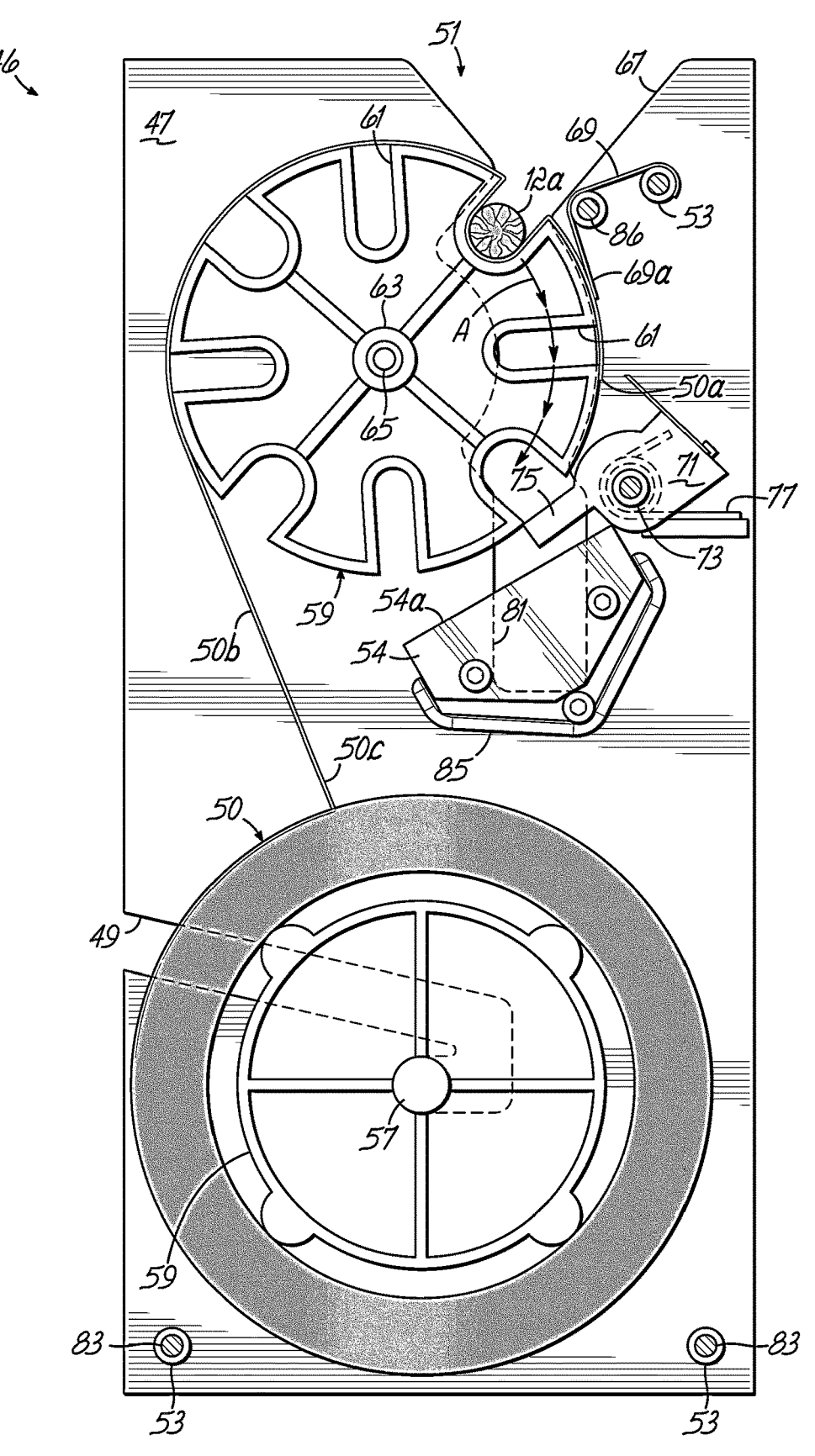

An arcuate portion 79 of the bag seal notch 51 is continuous with the throat 67 and follows the arc of the circumference of the sealing spool 59. A terminal cutting portion 81 of the bag seal notch 51 is continuous with the arcuate portion 79. A number of screws or other fasteners 83 secure the plates 47, 47 to the components of the cartridge 46. As seen in FIG. 15, a cutter 54 is mounted by a bracket 85 just below the keeper arm 75. The cutter 54 has an upwardly oriented cutting edge 54a which spans the cutting portion 81 of the bag seal notch 51.

Figure 7A:
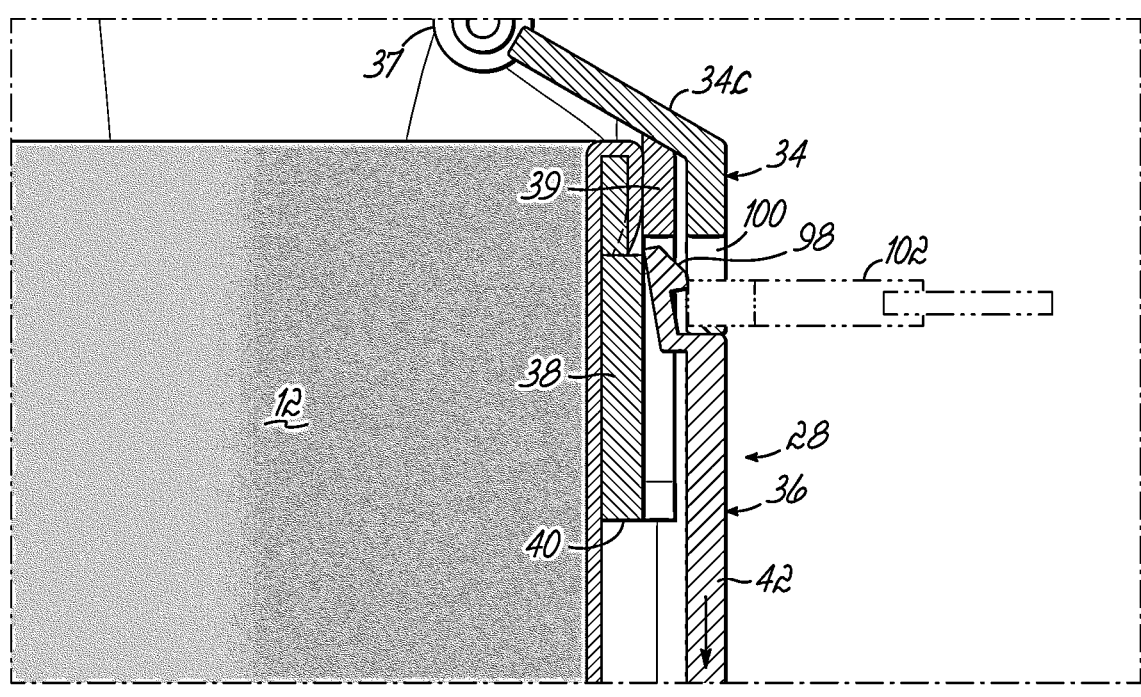
FIGS. 7A-7B are sequential side elevational cross-sectional views showing the receptacle being released from the collapsed configuration to an expanded configuration.
Figure 7B:
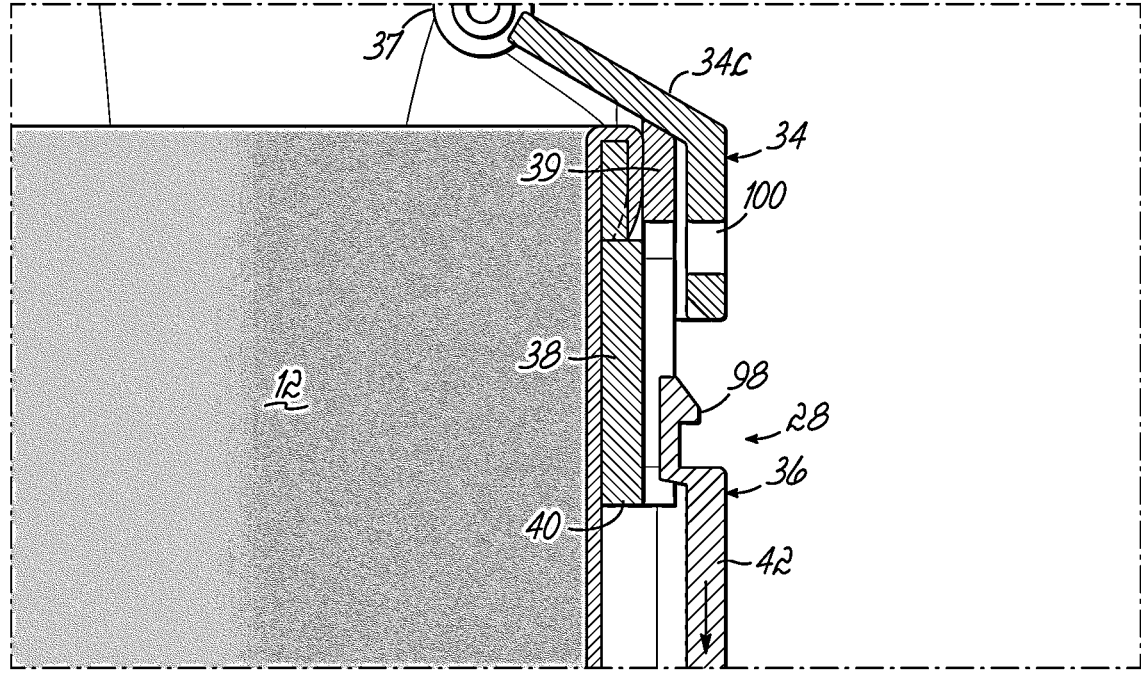

The body assembly 28 may be converted to and between the collapsed configuration of FIG. 2 and the expanded configuration of FIG. 9. In one embodiment of the receptacle 10, the shell 42 may translate downwardly from the collapsed configuration to the expanded configuration and upwardly from the expanded configuration to the collapsed configuration. The movement of the shell 42 in this regard is guided by a pair of rack gears 86 (FIG. 3) each mounted on an upright portion 88 of the bracket 44 adjacent to a terminal side curved edge 90 of the upright portion 88. As seen in FIGS. 3 and 8A-8B, a pair of pinion gears 92 are each mounted for rotation to a one of a pair of braces 94 proximate one of the terminal side edges 96 of the shell 42. Each pinion gear 92 meshes with and travels along one of the rack gears 86 to guide and facilitate the vertical movement of the bracket 44 relative to the shell 42. A detent hook 98 extends upwardly from a top edge of the shell 42 and is seated within a pocket 100 on the collar 34 to releasably secure the shell 42 and bracket 44 in the collapsed configuration. As shown in FIGS. 7A-7B, a tool 102 may be inserted into the pocket 100 to deflect the detent hook 98 and release the shell 42 for downward movement into the expanded configuration.

FIGS. 5-17 show a series of sequential views of using and servicing the disposal receptacle 10 of this embodiment. The bag 12 is in the receptacle 10 in the collapsed configuration with the lid 32 closed in FIG. 5. A user may depress the forward portion of the lid 32 to pivot the lid 32 about the hinge 37 and open the lid 32 for a soiled product 104 to be deposited through the open lid 32 and into the bag 12 in the body assembly 28 as in FIG. 6. Note that the lid 32 when pivoted to the open position blocks the view of the interior of the receptacle 10 and the contents of the bag 12 from a user's view.

Figure 8:
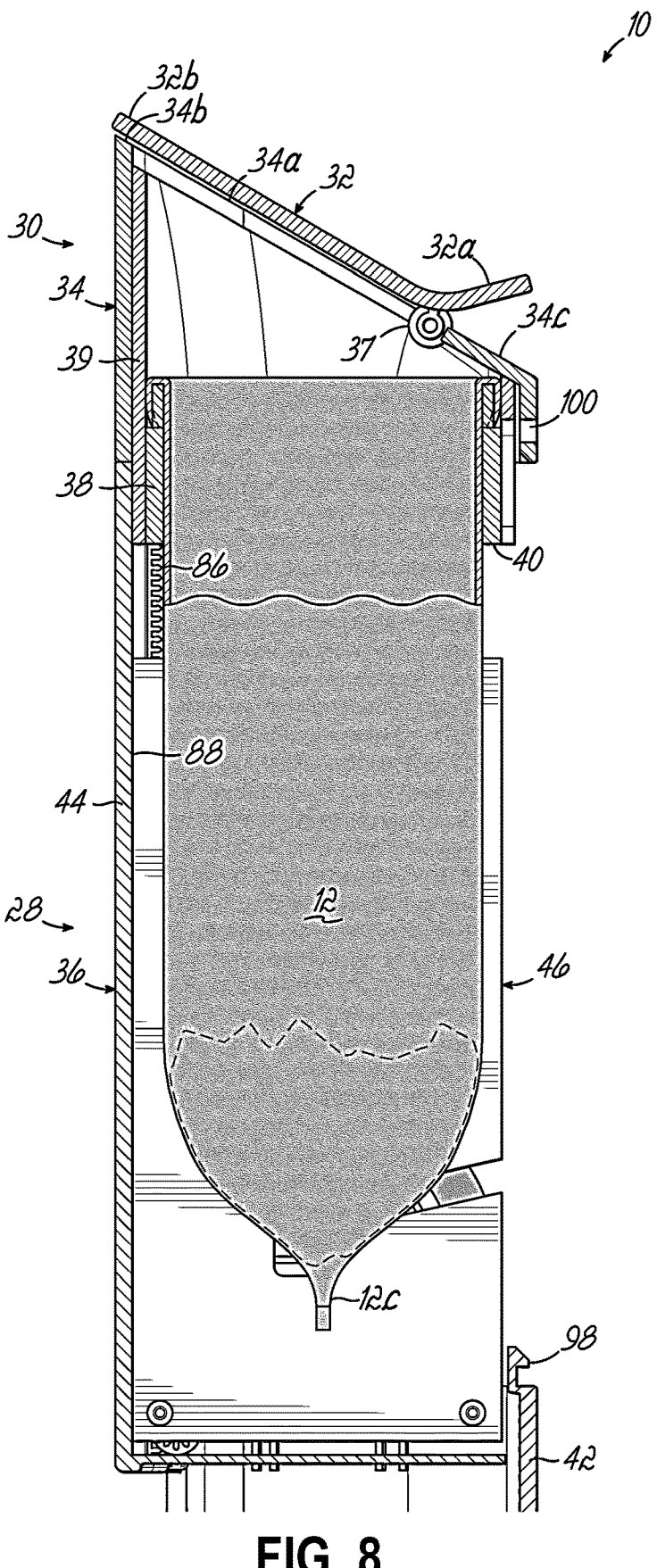
FIG. 8 is a view similar to FIG. 5 with the receptacle in an expanded configuration.
Figure 8A:
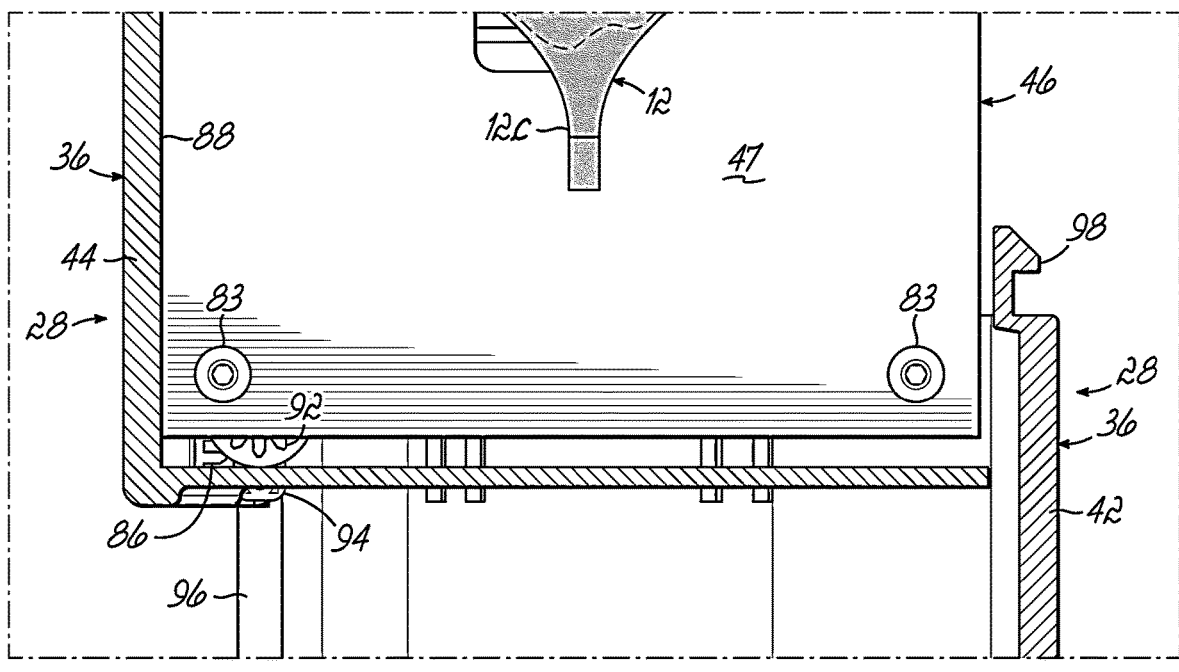
FIGS. 8A-8B are similar side elevational cross-sectional views showing the movement of the disposal receptacle.
Figure 8B:
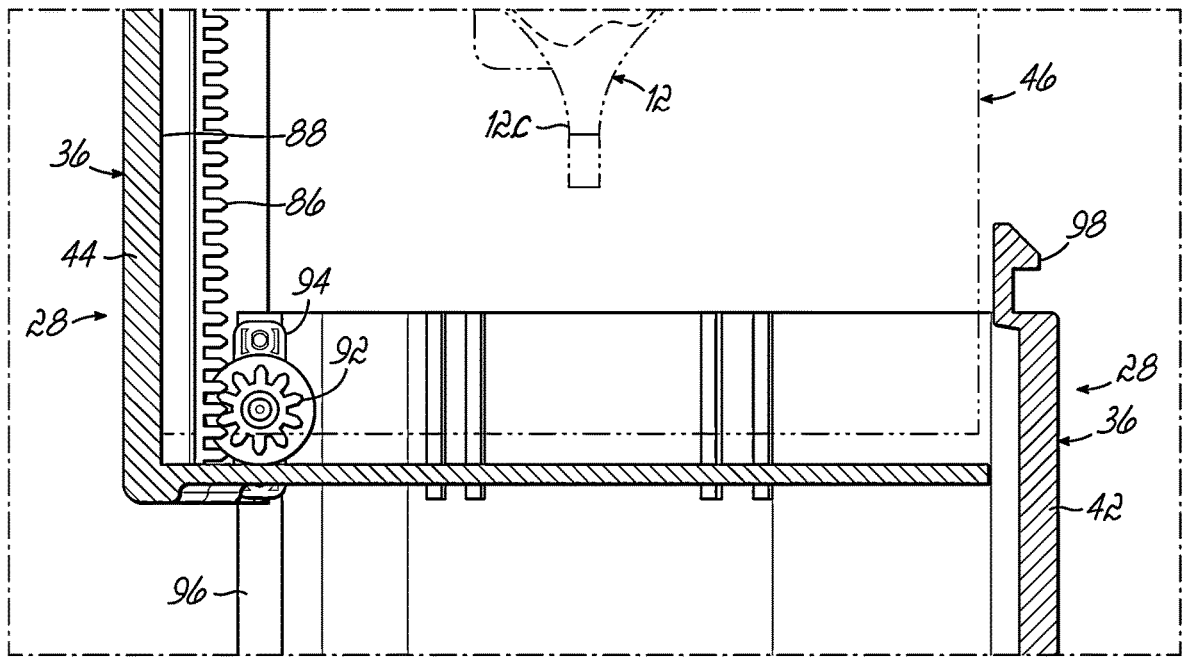
Figure 11:
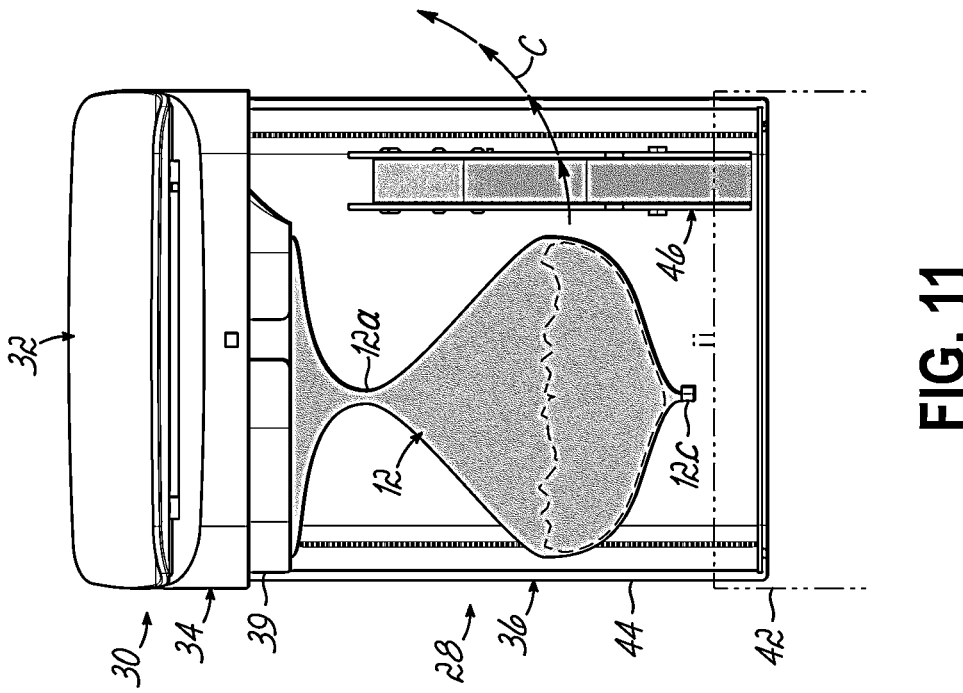
FIGS. 10-13 are front elevational cross-sectional views showing a filled bag being sealed and removed from the disposal receptacle according to one embodiment of this invention.
Figure 10:
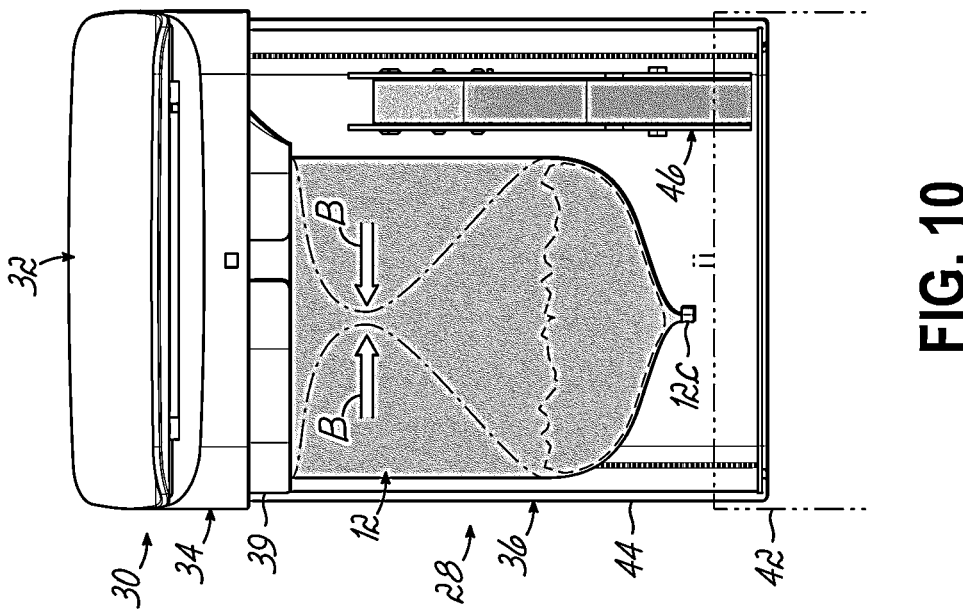
Figure 12:
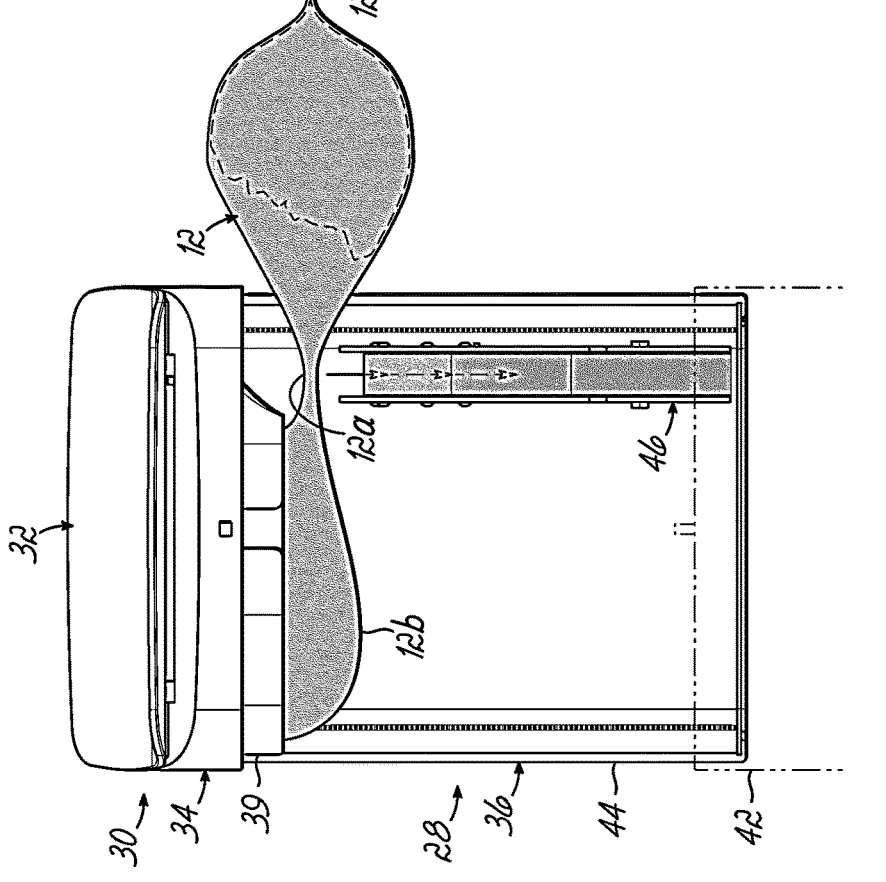

As shown in FIG. 7, when the bag 12 is filled and/or needs to be removed, a custodian or other service personnel may transform the receptacle 10 into the expanded configuration by inserting the tool 102 into the pocket 100 (FIG. 7A) to deflect the hook 98 (FIG. 7B) and release the shell 42 downwardly relative to the bracket 44 as seen in FIG. 8. The movement of the shell 42 is controlled by the rack 86 and pinion 92 gears as shown in FIGS. 8A-8B. The filled bag 12 is accessible when the receptacle is in the expanded configuration as shown in FIG. 9. Likewise, the cartridge 46 is exposed in the expanded configuration. The upper portion 12a of the filled bag 12 can then be gathered and collapsed as shown by arrows B in FIG. 10. As shown in FIG. 11, the filled bag 12 can then be swung in the direction arrows C toward the cartridge 46 and the upper collapsed portion 12a aligned over the throat 67 of the bag seal notch 51 of the cartridge 46 (FIG. 12).

Figure 13:
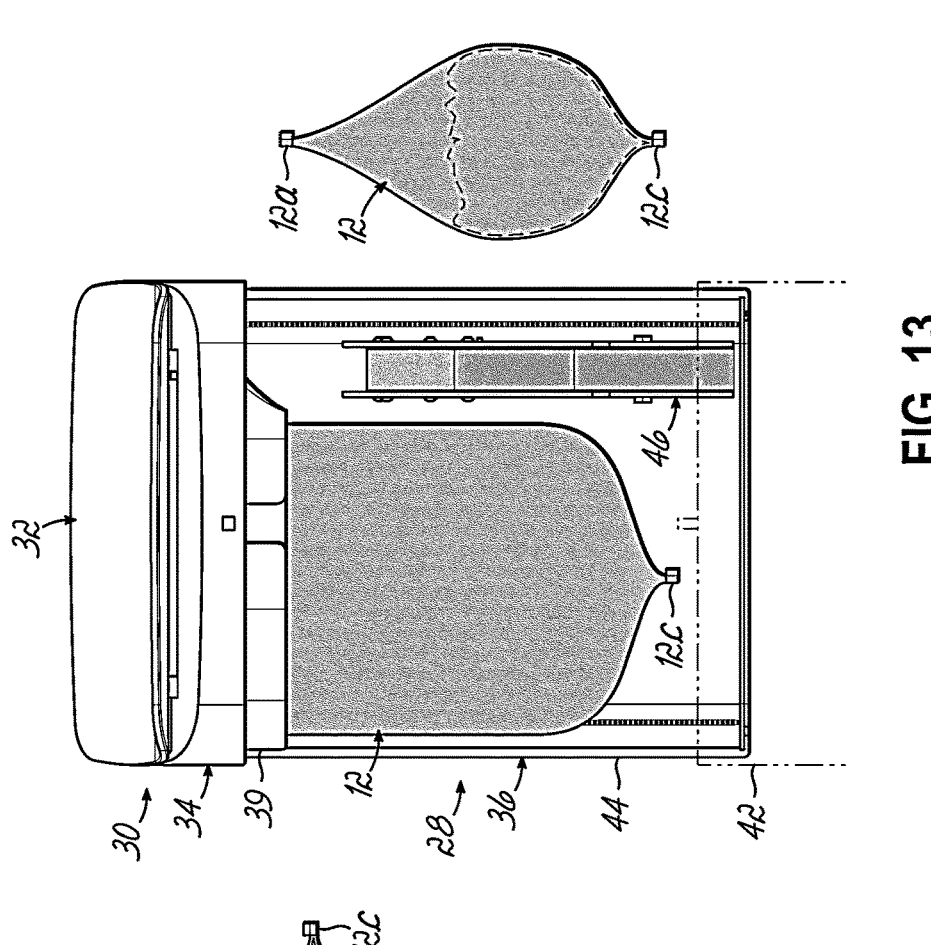

The operator then forces the upper collapsed portion 12a of the filled bag 12 downwardly through the throat 67, arcuate portion 79 and cutting portion 81 of the bag seal notch 51 to seal the top of the filled bag 12 sever the filled and sealed bag 12 from the remainder of the supply of bag material 12b. The tape 50 which wraps around the upper portion 12a of the filled bag 12 seals the filled bag 12 for disposal. The tape 50 is wrapped around the bag 12 also seals the bottom end 12c for the subsequent bag 12. The wrapped tape 5o is cut by the cutter 54 in the cartridge 46 so that a portion seals the top of the filled bag 12 and a portion of the wrapped tape seals the bottom the subsequent bag 12 and the receptacle 10 can be returned to the collapsed configuration for continued use (FIG. 13).

Figure 14:
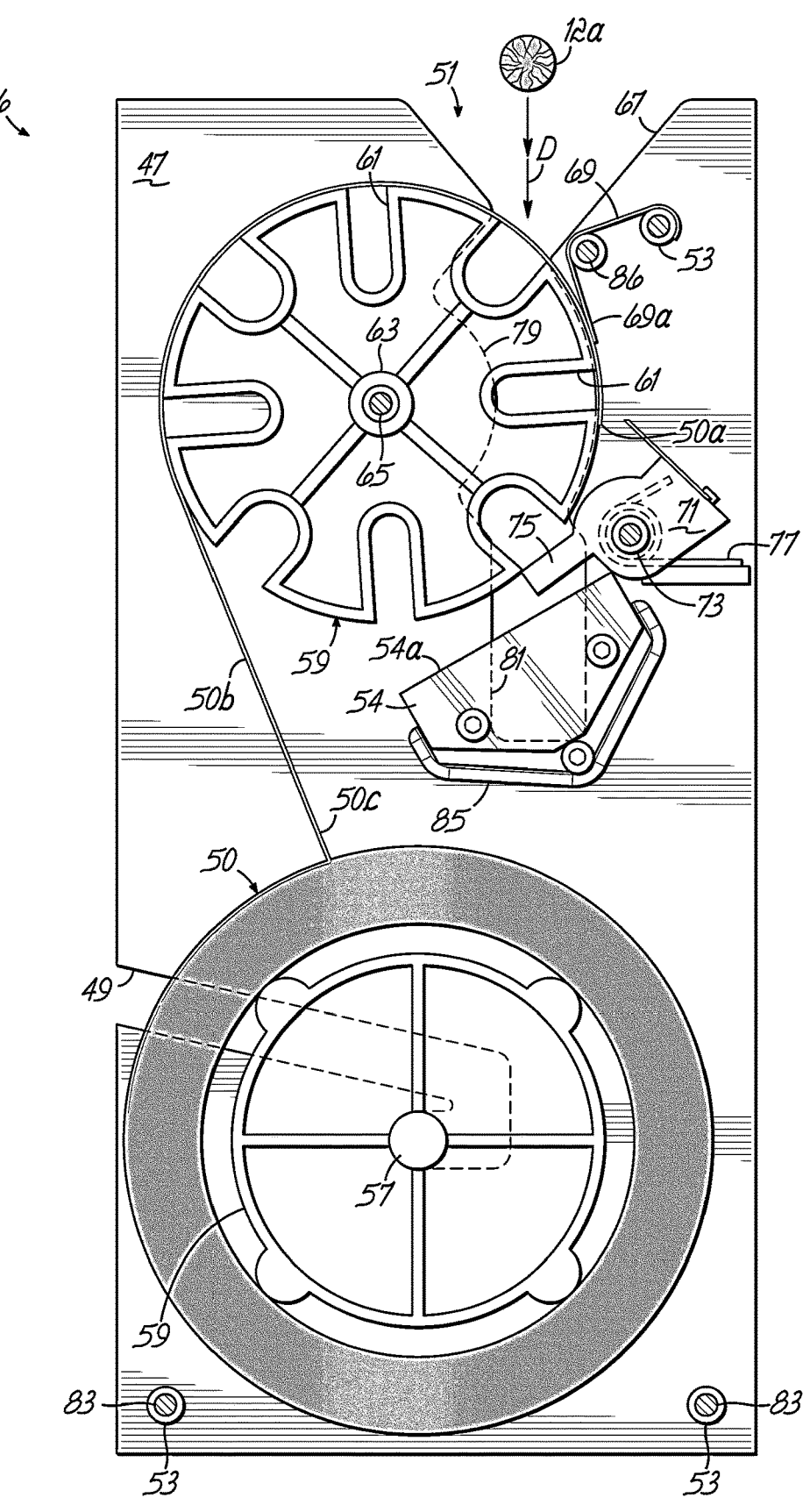
FIGS. 14-17 are sequential side elevational views of the filled bag being sealed and severed for removal from the disposal receptacle for disposal.
Figure 16:
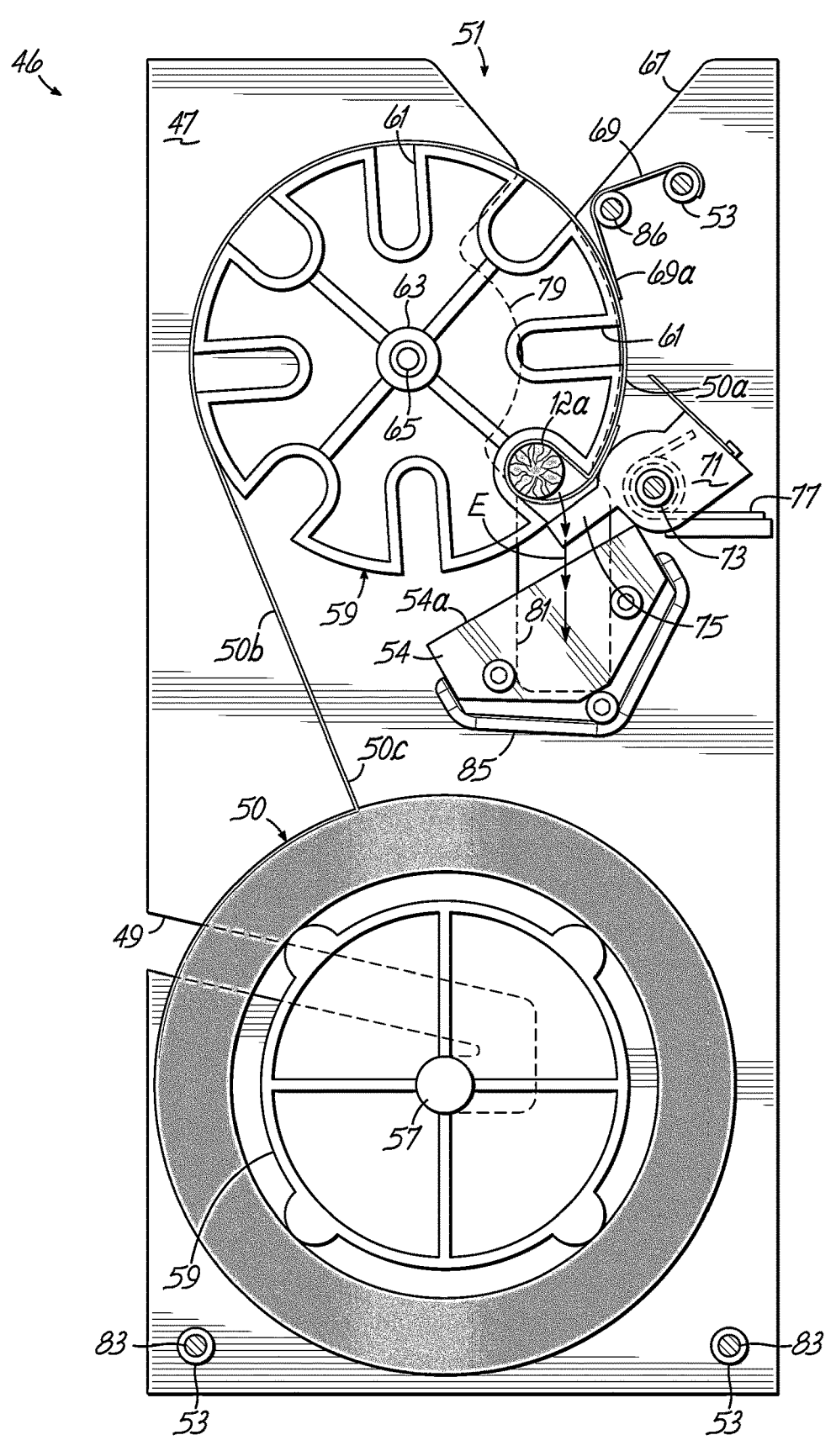

The operation of the cartridge 46 is more clearly shown in FIGS. 14-17. The upper collapsed portion 12a of the filled bag 12 is forced downwardly by a user in the direction of arrow D into the throat 67 of the bag seal notch 51 in the plates 47, 47 as shown in FIG. 14. The upper collapsed portion 12a of the bag 12 is received into one of the notches 61 in the sealing spool 59 and in so doing contacts the adhesive face 50b of the tape 50 on the circumference of the sealing spool 59 covering the notch 61. As shown in FIG. 15, the user continues to force the upper portion 12a downwardly through the arcuate portion 79 of the bag seal notch 51 and thereby rotating the sealing spool 59 in the direction of arrows A. Further downward movement of the upper portion 12a seated in the notch 61 positions the notch 61 and upper portion 12a adjacent the keeper arm 75 and at the beginning of the cutting portion 81 of the bag seal notch 51 as shown in FIG. 16. The adhesive face 50b of the tape 50 continues to wrap around the upper portion 12a of the bag 12.

Figure 17:
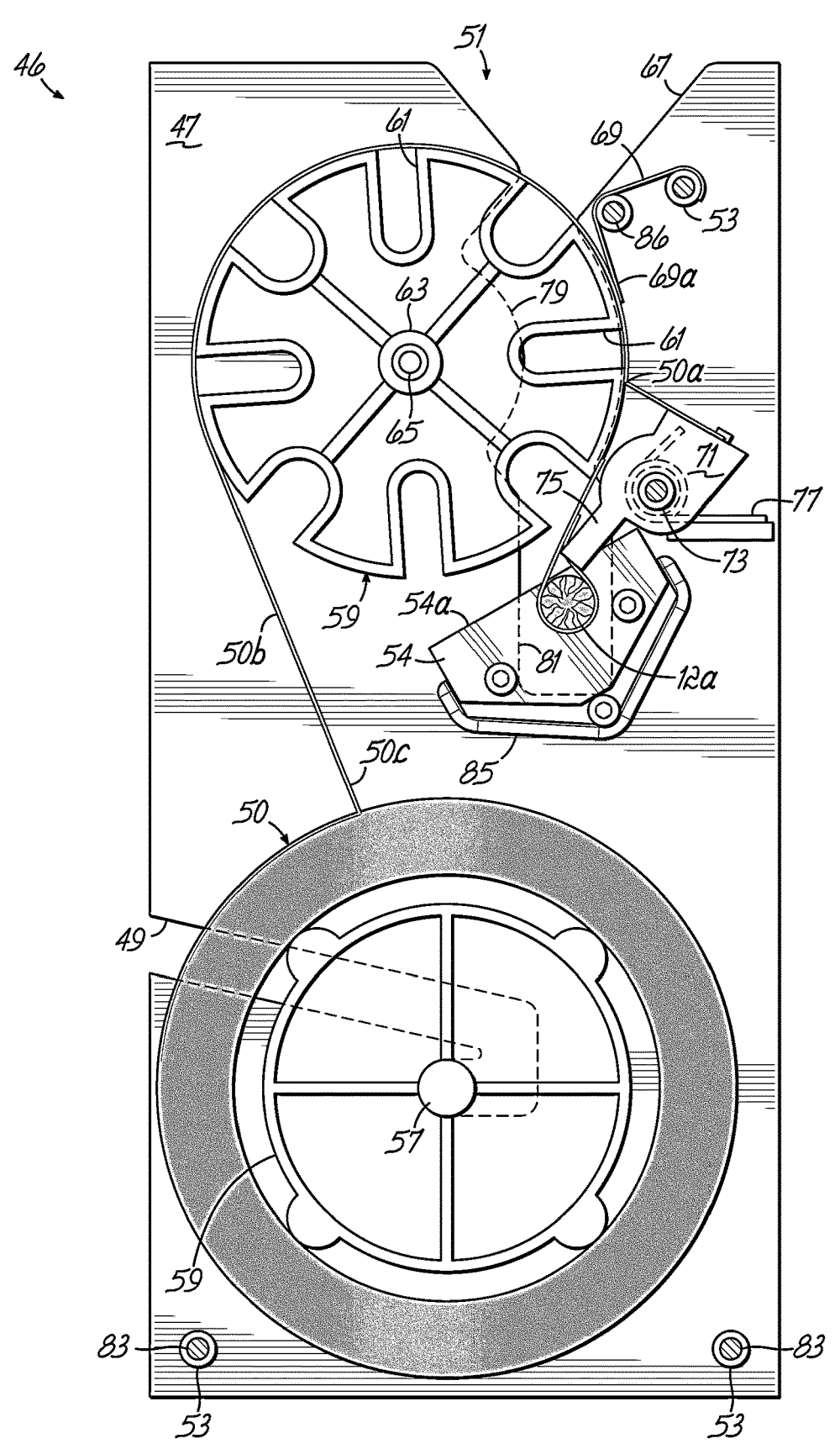

Further downward movement of the upper portion 12a within the cutting portion 81 in the direction of arrows E in FIG. 16 pivots the keeper arm 75 downwardly to allow the upper portion 12a to exit the notch 61 while the keeper arm 75 forces the tape 50 around the upper portion 12a to form a tight wrap therearound. Further downward movement of the upper portion 12a in the cutting portion 81 of the notch 51 forces the tape wrapped upper portion 12a against the cutting edge 54a of the cutter 54 as shown in FIG. 17. The tape wrapped upper portion 12a is cut by the cutter 54 to approximately bisect the tape 50 around the upper portion 12a. As a result, a first cut portion of the severed tape 50 around the upper portion 12a seals the filled bag 12 for disposal. A second cut portion of the severed tape 50 forms a bottom sealed end 12c of the subsequent bag 12 for use in the receptacle 10. A supply of bag material 12b in a tubular configuration is housed in the rim 38 and the distal end of the bag material 12b is pulled from the supply housed in the rim 38 to form the bottom of the bag 12 to be filled in the receptacle 10 as described.

When the tape 50 is depleted, the empty tape roll and supply spool 59 may be removed from the cartridge 46 via the tape notch 49 in the plates 47, 47 and new roll of tape 50 may be installed on the spool 59 and returned to the end of the tape notch 49 in the cartridge 46.

As the filled bag 12 is pulled, the top end 12a of the filled bag 12 is cut and sealed by the cutter 54 in the cartridge. The cartridge 46 simultaneously cuts and seals the filled bag 12 and seals a bottom end 12c of the adjacent bag 12 on supply of bag material housed in the body assembly 28. As the bags are pulled through the throat 52, tape 50 is wrapped around the gathered top of the filled bag 12 and the gathered bottom of the subsequent bag 12 to thereby seal the bags 12.

According to various embodiments of this invention, the process of removal of the filled bag 12 and replacement with a subsequent bag 12 reduces process steps for limiting the learning curve, time and effort for servicing the receptacle 10 of this invention.

The various features and components of the disclosed embodiments of this invention may be used in various combinations to provide an aesthetically pleasing receptacle 10 which minimizes the exposure to the soiled products therein and the escape of foul odors emanating therefrom.

From the above disclosure of the general principles of this invention and the preceding detailed description of at least one embodiment, those skilled in the art will readily comprehend the various modifications to which this invention is susceptible. Therefore, we desire to be limited only by the scope of the following claims and equivalents thereof.

We claim:

1. A receptacle for soiled feminine care products adapted to be mounted to a wall, the receptacle comprising:
    a body assembly comprising:
        a shell,
        a bracket comprising a back wall, wherein the shell and the bracket are configured to move relative to each other between a collapsed configuration and an expanded configuration,
        a rack and a pinion operatively engaged with each other, wherein the rack and the pinion are configured to guide and facilitate movement of the shell and the bracket relative to each other between the collapsed configuration and the expanded configuration, and
        an open upper end;
    a bag within the body assembly, wherein the bag is configured to receive soiled feminine care products; and
    a lid pivotally coupled to the body assembly about a pivot axis; wherein
    the lid comprises a lever portion;
    the lid is configured to pivot about the pivot axis between a closed position and an open position;
    the lid, while in the closed position, covers the open upper end of the body assembly:
    the lid, while in the open position, is configured to allow for soiled feminine care products to be deposited into the bag within the body assembly;
    the open position is formed between the lid and an upper edge of the back wall of the body assembly;
    the pivot axis is interposed between the lever portion and the back wall such that the lever portion is configured to be depressed to thereby pivot the lid toward the open position;
    while the body assembly is in the collapsed configuration, the bag is concealed in the body assembly; and
    while the body assembly is in the expanded configuration and the lid remains in the closed position, the bag and soiled feminine products are removable from the receptacle.

2. The receptacle of claim 1 further comprising:
    a hinge spaced from the back wall and coupling the lid to the body assembly for movement to and from the open and closed positions such that the lid at least partially blocks viewing access to the bag when in the open position.

3. The receptacle of claim 1 wherein the lid is oriented obliquely relative to the back wall when in the closed position.

4. The receptacle of claim 1 wherein the lever portion extends forwardly and in a different plane from a remainder of the lid.

5. A receptacle for soiled feminine care products adapted to be mounted to a wall, the receptacle comprising:
    a body assembly comprising:
        a shell,
        a bracket, wherein the shell and the bracket are movable relative to each other between a collapsed configuration and an expanded configuration,
        a pair of racks fixed to and extending vertically along the bracket,
        a pair of pinions associated with the shell, wherein each pinion of the pair of pinions is operatively engaged with a respective rack of the pair of racks in order to facilitate movement of the shell and the bracket relative to each other between the collapsed configuration and the expanded configuration, and
        an open portion;
    a bag removably housed within the body assembly, wherein the bag defines an interior, wherein the interior of the bag is dimensioned to receive therein soiled feminine care products; and
    a lid assembly coupled to the body assembly;
    wherein the lid assembly is configured move between a closed position and an open position;
    the lid assembly, while in the closed position, covers the open portion of the body assembly and the interior of the bag;
    the lid assembly, while in the open position, is configured to allow for soiled feminine products to be deposited into the bag within the body assembly;
    the body assembly is configured to conceal the bag in the body assembly while in the collapsed configuration; and
    the body assembly is configured to accommodate removal of at least a portion of the bag and soiled feminine products therein when the body assembly is in the expanded configuration and the lid assembly is in the closed position such that the interior of the bag remains covered.

6. The receptacle of claim 5 further comprising:
    a cartridge in the body assembly adapted to seal an open end of the bag when the body assembly is in the expanded configuration.

7. The receptacle of claim 6 further comprising:
    a supply of bag material in the body assembly from which the bag is formed from a distal portion of the supply of bag material.

8. The receptacle of claim 7 further comprising:
    a cutter adapted to separate the bag containing the soiled feminine products from a remainder of the supply of bag material.

9. The receptacle of claim 8 wherein the cartridge further comprises the cutter.

10. The receptacle of claim 5 further comprising:
    a cartridge on the bracket adapted to seal an open end of the bag when the body assembly is in the expanded configuration;
    a supply of bag material in the body assembly from which the bag is formed from a distal portion of the supply of bag material; and
    a cutter adapted to separate the bag containing the soiled feminine products from the supply of bag material.

11. The receptacle of claim 10 wherein the cartridge further comprises:
    the cutter; and
    a roll of tape from which a terminal portion of the roll of tape is positioned in the cartridge to be wrapped around a portion of the bag containing the soiled feminine products, the terminal portion of the roll of tape sealing both a top of the bag containing soiled feminine products being removed from the receptacle and sealing a bottom of a subsequent bag for use in the receptacle after being cut by the cutter.

12. The receptacle of claim 5 wherein the shell and the bracket move relative to one another along a longitudinal axis of the receptacle, the receptacle further comprising:

a cartridge in the body assembly adapted to seal an open end of the bag oriented generally perpendicular to the longitudinal axis and when the body assembly is in the expanded configuration.

* * * * *